(12) United States Patent
Santello et al.

(10) Patent No.: US 10,849,532 B1
(45) Date of Patent: Dec. 1, 2020

(54) COMPUTER-VISION-BASED CLINICAL ASSESSMENT OF UPPER EXTREMITY FUNCTION

(71) Applicants: Marco Santello, Gilbert, AZ (US); Yezhou Yang, Tempe, AZ (US); Qiushi Fu, Chandler, AZ (US)

(72) Inventors: Marco Santello, Gilbert, AZ (US); Yezhou Yang, Tempe, AZ (US); Qiushi Fu, Chandler, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 67 days.

(21) Appl. No.: 16/214,847

(22) Filed: Dec. 10, 2018

Related U.S. Application Data

(60) Provisional application No. 62/596,652, filed on Dec. 8, 2017.

(51) Int. Cl.
  *A61B 5/11* (2006.01)
  *A61B 5/107* (2006.01)

(52) U.S. Cl.
  CPC .......... *A61B 5/1125* (2013.01); *A61B 5/1071* (2013.01); *A61B 5/1079* (2013.01);
  (Continued)

(58) Field of Classification Search
  None
  See application file for complete search history.

(56) References Cited

U.S. PATENT DOCUMENTS

| 9,619,105 | B1 * | 4/2017 | Dal Mutto | ............ G06F 3/0304 |
| 2010/0053151 | A1 * | 3/2010 | Marti | ...................... G06F 3/017 |
| | | | | 345/419 |

(Continued)

FOREIGN PATENT DOCUMENTS

| WO | 2015172096 A1 | 11/2015 |
| WO | 2017147041 A1 | 8/2017 |

OTHER PUBLICATIONS

Butt, A. et al., "Leap motion evaluation for assessment of upper limb motor skills in Parkinson's disease", 2017 International Conference on Rehabilitation Robotics (ICORR) [London, UK, Jul. 17-20, 2018], 2017 [date added to IEEE Xplore Aug. 2017], pp. 116-121, <DOI:10.1109/ICORR.2017.8009232>.

(Continued)

*Primary Examiner* — Kevin Ky
(74) *Attorney, Agent, or Firm* — Michael Best & Friedrich LLP

(57) ABSTRACT

Methods and systems are presented for kinematic tracking and assessment of upper extremity function of a patient. A sequence of 2D images is captured by one or more cameras of a patient performing an upper extremity function assessment tasks. The captured images are processed to separately track body movements in 3D space, hand movements, and object movements. The hand movements are tracked by adjusting a position, orientation, and finger positions of a three-dimensional virtual model of a hand to match the hand in each 2D image. Based on the tracked movement data, the system is able to identify specific aspects of upper extremity function that exhibit impairment instead of providing only a generalized indication of upper extremity impairment.

20 Claims, 9 Drawing Sheets

(52) U.S. Cl.
CPC ........... *A61B 5/1114* (2013.01); *A61B 5/1121* (2013.01); *A61B 5/1128* (2013.01)

(56) References Cited

U.S. PATENT DOCUMENTS

| | | | |
|---|---|---|---|
| 2010/0128112 A1* | 5/2010 | Marti | G06F 3/011 348/51 |
| 2011/0221656 A1* | 9/2011 | Haddick | G02B 27/0172 345/8 |
| 2012/0158437 A1* | 6/2012 | Little | G06Q 40/08 705/4 |
| 2014/0022171 A1* | 1/2014 | Yanai | G06F 3/017 345/158 |
| 2014/0085625 A1* | 3/2014 | Ahmed | G06K 9/00362 356/73 |
| 2014/0211991 A1* | 7/2014 | Stoppa | G06K 9/00355 382/103 |
| 2014/0347479 A1* | 11/2014 | Givon | H04N 21/4415 348/143 |
| 2015/0089453 A1* | 3/2015 | Dal Mutto | G06F 3/0304 715/852 |
| 2016/0140865 A1 | 5/2016 | Marzetti et al. | |
| 2016/0253044 A1* | 9/2016 | Katz | G06F 3/04842 345/156 |
| 2016/0295168 A1* | 10/2016 | Rangan | G09B 5/14 |
| 2017/0242483 A1* | 8/2017 | Goslin | G06F 3/014 |
| 2017/0262045 A1* | 9/2017 | Rouvinez | G06F 3/011 |
| 2017/0265784 A1 | 9/2017 | Santello | |
| 2017/0348854 A1* | 12/2017 | Oleynik | A47J 47/02 |
| 2019/0018567 A1* | 1/2019 | Murphy | G06F 3/012 |
| 2019/0054277 A1 | 2/2019 | LaBelle et al. | |
| 2019/0069796 A1 | 3/2019 | Santello et al. | |
| 2019/0167504 A1 | 6/2019 | Polygerinos et al. | |
| 2019/0303090 A1* | 10/2019 | Milne | H04S 3/008 |
| 2020/0042111 A1* | 2/2020 | Connellan | G02B 27/0172 |

OTHER PUBLICATIONS

Cruz, L. et al., "Kinect and RGBD Images: Challenges and Applications", 25th SIBGRAPI Conference on Graphics, Patterns and Images Tutorials (Ouro Preto, Brazil, Aug. 22-25, 2012), 2012 [date added to IEEE Xplore Dec. 2012], pp. 36-49, <DOI:10.1109/SIBGRAPI-T.2012.13>.

Kim, W. et al., "Upper Extremity Functional Evaluation by Fugl-Meyer Assessment Scoring Using Depth-Sensing camera in Hemiplegic Stroke Patients", PLoS One, Jul. 2016, vol. 11, No. 7, article e0158640, 13 pages <DOI:10.1371/journal.pone.0158640>.

Van Dijck, G. et al., "Posterior probability profiles for the automated assessment of the recovery of patients with stroke from activity of daily living tasks", Artificial Intelligence in Medicine, Jul. 2009, [available online May 2009], vol. 16, No. 3, pp. 233-249 <DOI:10.1016/tartmed.2009.03.001>.

Wade, E et aL, "Automated administration of the Wolf Motor Function Test for post-stroke assessment", 2010 4th International Conference on Pervasive Computing Technologies for Healthcare (Munich, Germany, Mar. 22-25, 2010), Jun. 2010, 7 pp. <DOI:10.4108/Icst.PERVASIVEHEALTH2010.8903>.

Wade, E et al., "Virtual Reality and Robotics for Stroke Rehabilitation: Where Do We Go from Here?", Topics in Stroke Rehabilitation, Dec. 2011, vol. 18, No. 6, pp. 685-700 <DOI:10.1310/TSR1806-685>.

Walter, S. et aL, "Sample size and optimal designs for reliability studies", Statistics in Medicine, Jan. 1998, vol. 17, No. 1, pp. 101-110 <DOI:10.1002/(sici)1097-0258(19980115)17:1<101::aid-sim727>3.0.co;2-e>.

Wang, L et aL, "Learning and matching of dynamic shape manifolds for human action recognition", IEEE Transactions on Image Processing, Jun. 2007 [IEEE Date of Publication: May 2017], vol. 16, No. 6, pp. 1646-1661 <DOI:10.1109/Tip.2007.896661>.

Wei, S.-E. et al., "Convolutional pose machines", IEEE Intenational Conference on Computer Vision and Pattern Recognition (Las Vegas, Nevada, Jun. 27-30, 2016), 2016 [Date Added to IEEE Xplore: Dec. 2016], pp. 1724-4732 <DOI:10.1109/CVPR.2016.511>.

Wei, S.-E. et al., "Convolutional pose machines", arXiv, v1, submitted Jan. 30, 2016, 9 pages, https://arxiv.org/abs/1602.00134v1.

Wei, S.-E. et al., "Convolutional pose machines", arXiv, v2, submitted Feb. 2, 2016, 9 pages, https://arxiv.org/abs/1602.00134v2.

Wei, S.-E. et al., "Convolutional pose machines", arXiv, v3, submitted Mar. 28, 2016, 9 pages, https://arxiv.org/abs/1602.00134v3.

Wei, S.-E. et al., "Convolutional pose machines", arXiv, v4, submitted Apr. 12, 2016, 9 pages, https://arxiv.org/abs/1602.00134v4.

Welmer, a. et al., "Limited tine hand use after stroke and its association with other disabilities", Journal of Rehabilitation Medicine, Aug. 2008, vol. 40, No. 8, pp. 603-608 <DOI:10.2340/16501977-0218>.

Willems, G. et al., "An efficient dense and scale-invariant spatio-temporal interest point detector", European conference on Computer Vision (Marseille, France, Oct. 12-18, 2008), pp. 650-663 <DOI:10.1007/978-3-540-88688-4_48>.

Yang, Y. et al., "A Cognitive System for Understanding Human Manipulation Actions", Advances in Cognitive Systems, Aug. 2014, vol. 3, pp. 67-86.

Yang, Y. et al., "Detection of manipulation action consequences (MAC)", IEEE Conference on Computer Vision and Pattern Recognition (Portland, Oregon, Jun. 23-28, 2013), 2013 [Date Added to IEEE Xplore: Oct. 2013], pp. 2563-2570 <DOI:10.1109/CVPR.2013.331>.

Yang, Y. et al., "Grasp Type Revisited: A Modern Perspective on a Classical Feature for Vision", 2015 IEEE Intenational Conference on Computer Vision and Pattern Recognition (Boston, Massachusetts, 2015), 2015 [Date Added to IEEE XPlore: Oct. 2015], pp. 400-408 <DOI:10.1109/CVPR.2015.7298637>.

Yang, Y. et al., "Learning the Semantics of Manipulation Action", 53rd Annual Meeting of the Association for computational Linguistics (Beijing, China, Jul., 2015), pp. 676-686 <DOI:10.3115/v1/P15-1066>.

Yang, Y. et al., "Robot Learning Manipulation Action Plans by "Watching" Unconstrained Videos from the World Wide Web", the Twenty-Ninth AAAI Conference on Artificial Intelligence (Austin, Texas, Jan. 25-30, 2015), Jan. 2015, pp. 3686-3692.

Yang, Y. et al., "Robots with language: Multi-label visual recognition using Nlp", IEEE International Conference on Robotics and Automation (Karlsruhe, Germany, May 6-10, 2013), 2013 [Date Added to IEEE Xplore: Oct. 2013], pp. 4256-4262 <DOI:10.1109/ICRA.2013.6631179>.

Yozbatiran, N. et al., "A Standardized Approach to Performing the Action Research Arm Test", Neurorehabilitation and Neural Repair, Jan.-Feb. 2008, [available online Aug. 2007],vol. 22, No. 1, pp. 78-90 <DOI:10.1177/1545968307305353>.

Zhang, M. et aL, "Beyond the standard clinical rating scales: Fine-grained assessment of post-stroke motor unctionality using wearable inertial sensors", 2012 Annual International Conference of the IEEE Engineering in Medicine and Biology Society (San Diego, California, Aug. 28- Sep. 1, 2012), 2012 [Date Added to IEEE Kplore: Nov. 2012], pp. 6111-6115 <DOI:10.1109/EMBC.2012.6347388>.

Zipp, G. et al., "StrokEDGE Taskforce", Neurology Section, Aug. 2010, 278 pages.

Zou, G., "Sample size formulas for estimating intraclass correlation coefficients with precision and assurance", Statistics in Medicine, Jul. 2012, vol. 31, pp. 3972-3981 <DOI.10.1002/sim.5466>.

Balasubramanian, S. et al., "Robot-measured performance metrics in stroke rehabilitation", 2009 ICME Intenational Conference on Complex Medical Engineering (Tempe, Arizona, May 11, 2009), May 2009, pp. 1-6 <DOI:10.1109/Iccme.2009.4906654>.

Beebe, J. et al., "Relationships and responsiveness of six upper extremity function tests during the first 6 months of recovery after stroke", Journal of Neurologic Physical Therapy, Jun. 2009, vol. 33, No. 2, pp. 96-103 <DOI:10.1097/ 1PT.0b013e3181a33638>.

(56) References Cited

OTHER PUBLICATIONS

Benjamin, E. et al., "Heart Disease and Stroke Statistics-2017 Update: A Report From the American Heart Association", Circulation, Mar. 2017, vol. 135, pp. e146-e603 <DOI:10.1161/Cir.0000000000000485>_.

Calinsky, T. et al., "A dendrite method for cluster analysis", Communications in Statistics, Jan. 1974, [available Wine Jun. 1974], vol. 3, pp. 1-27 <DOI:10.1080/03610927408827101>.

Cao, Z. et al., "Realtime Multi-Person 2D Pose Estimation using Part Affinity Fields", 2017 IEEE Intenational conference on Computer Vision and Pattern Recognition (Honolulu, Hawaii, Jul. 21-26, 2017), 2017 [Date added to IEEE Xplore: Nov. 2017], pp. 1302-1310 <DOI:10.1109/Cvpr.2017.143>.

Cao, Z. et al., "Realtime Multi-Person 2D Pose Estimation using Part Affinity Fields", arXiv, v1, submitted Nov. 24, 2016, 9 pages, https://arxiv.org/abs/1611.08050v1.

Cao, Z. et al., "Realtime Multi-Person 2D Pose Estimation using Part Affinity Fields", arXiv, v2, submitted Apr. 14, 2017, 9 pages, https://arxiv.org/abs/1611.08050v2.

Carpinella, L et al., "Quantitative assessment of upper limb motor function in Multiple Sclerosis using an nstrumented Action Research Arm Test", Journal of Neuroengineering and Rehabilitation, Apr. 2014, vol. 11, No. 67, 16 pages <DOI:10.1186/1743-0003-11-67>.

Chang, C.-Y. et al., "Towards Pervasive Physical Rehabilitation Using Microsoft Kinect", 2012 6th International conference on Pervasive Computing Technologies for Healthcare (PervasiveHealth) and Workshop (San Diego, California, May 21-24 2012), 2012, pp. 159-162 <DOI:10.4108/icst.pervasivehealth.2012.248714>.

Chang, L. L et aL, "Constrained least-squares optimization for robust estimation of center of rotation", Journal of Thomechanics, Jan. 2007, vol. 40, No. 6, pp. 1392-400 <DOI:10.1016/j.jbiomech.2006.05.010>.

Chang, L. et al., "Robust estimation of dominant axis of rotation", Journal of Biomechanics, Mar. 2007, vol. 40, No. 12, pp. 2707-2715 <DOI:10.1016/Hbiomech.2007.01.010>.

Chen, S. et al., "Discriminant validity of a new measure of self-efficacy for reaching movements after stroke-induced iemiparesis", Journal of Hand Therapy, Apr.-Jun. 2013, [available online Nov. 2012], vol. 26, No. 2, pp. 116-123 (2013 <DOI:10.1016/J.Jht.2012.09.002>.

Chen, X. et al., "Feasibility of using microsoft kinect to assess upper limb movement in type III Spinal muscular atrophy patients", PLoS One, Jan. 2017, vol. 12, pp. 1-12 <DOI:10.1371/joumal.pone.0170472>.

Cheung, V. et al., "Muscle synergy patterns as physiological markers of motor cortical damage", Proceedings of the National Academy of Sciences of the United States of America, Sep. 2012, [available online Aug. 2012], vol. 109, No. 36, pp. 14652-14656 <DOI:10.1073/pnas.1212056109>.

Dollar, P. et al., "Behavior recognition via sparse spatio-temporal features", 2nd Joint IEEE International Workshop on Visual Surveillance and Performance Evaluation of Tracking and Surveillance (Beijing, China, Oct. 15-16, 2005), 2005 [Date added to Xplore: Jan. 2006], pp. 65-72 <DOI:10.1109NSPETS.2005.1570899>.

Dukelow, S. et al., "Quantitative Assessment of Limb Postion Sense Following Stroke", Neurorehabilitation Neural Repair, Feb. 2010, [available online Sep. 2009], vol. 24, No. 2, pp. 178-187 <DOI:10.1177/1545968309345267>.

Fu, Q. et al., "Human reach-to-grasp compensation with object pose uncertainty", 35th Annual International IEEE Engineering in Medicine and Biology Society Conference (Osaka, Japan, Jul. 3-7, 2013), 2013 [Date Added to IEEE Xplore: Sep. 2013], pp. 6893-6896 <DOI:10.1109/Embc.2013.6611142>.

Fu, Q. et al., "Towards a complete description of grasping kinematics: a framework for quantifying human grasping and manipulation", Annual International Conference IEEE Engineering in Medicine and Biology Society (Boston, Vlassachusetts, Aug. 30-Sep. 3, 2011), 2011 [Date added to IEEE Xplore: Dec. 2011], pp. 8247-8250 <DOI:10.1109/1EMBS.2011.6092033>.

Fu, Q. et al., "Tracking whole hand kinematics using extended Kalman filter", 32nd IEEE Engineering in Medicine and Biology Society (Buenos Aires, Argentina, Aug. 31-Sep. 4, 2010), 2010 [Date Added to IEEE Xplore: Nov. 2010], pp. 4606-4609 <DOI:10.1109/Iembs.2010.5626513>.

Gavrila, D., "The visual analysis of human movement: a survey", Computer Vision and Image Understanding, Jan. 1999, vol. 73, No. 1, pp. 82- 98.

Gowland, C. et al., "Agonist and antagonist activity during voluntary upper-limb movement in patients with stroke", Physical Therapy, Sep. 1992, vol. 72, No. 9, pp. 624-633 <DOI:10.1093/Ptj/72.9.624>.

Grice, K. et al., "Adult Norms for a Commercially Available Nine Hole Peg Test for Finger Dexterity", American Journal of Occupational Therapy, Sep.-Oct. 2003, vol. 57, No. 5, pp. 570-573 <DOI:10.5014/ajot.57.5.570>.

Han, B. et al., "Visual tracking by continuous density propagation in sequential Bayesian filtering framework", IEEE Transactions on Pattern Analysis and Machine Intelligence, May 2009 [IEEE date of Publication: May 2008], vol. 31, No.. 5, pp. 919-930 <DOI:10.1109/TPAMI.2008.134>.

Han, B. et al., "Upper extremity 3-dimensional reachable workspace analysis in dystrophinopathy using Kinect", Muscle & Nerve, Sep. 2015 [available online Jan. 2015], vol. 52, No. 3, pp. 344-355 <DOI:10.1002/mus.24567>.

Herbert, J. et al., "Case report of modified Box and Blocks test with motion capture to measure prosthetic function", Journal of Rehabilitation Research and Development, 2012, vol. 49, No. 8, pp. 1163-1174 <DOI:10.1682/ JRRD.2011.10.0207>. no date available.

Hinton, G., "Reducing the Dimensionality of Data with Neural Networks", Science 28, Jul. 2013, vol. 313, Issue 5786, pp. 504-507 <DOI:10.1126/science_1127647>.

Hsueh, L et al., "Psychometric Comparisons of 2 Versions of the Fugl-Meyer Motor Scale and 2 Versions of the Stroke Rehabilitation Assessment of Movement", Neurorehabilitation and Neural Repair, Nov.-Dec. 2008, [available online Jul. 2008], vol. 22, No. 6, pp. 737-744 <DOI:10.1177/1545968308315999>.

Kinney, C. et al., "Standardization of Interdisciplinary Clinical Practice and Assessment in Stroke Rehabilitation", International Journal of Physical Medicine and Rehabilitation, Nov. 2013, vol. 1, No. 8, pp. 1-7 <DOI:10.4172/2329-9096.1000166>.

Lang, C. et al., "Assessment of upper extremity impairment, function, and activity after stroke: Foundations for clinical lecision making", Journal of Hand Therapy, Apr.-Jun. 2013, [available online Sep. 2012], vol. 26, No. 2, pp. 104-115 (2013)<DOI:10.1016/J.Jht.2012.06.005>.

Laptev, I., "On space-time interest points", International Journal of Computer Vision, Sep. 2005, vol. 64, No. 2-3, pp. 107-123 <DOI.10.1007/s11263-005-1838-7>.

Miathiowetz, V. et al., "Adult Norms for the Box and Block Test of Manual Dexterity", American Journal of occupational Therapy, Jun. 1985, vol. 39, pp. 386-391 <DOI:10.5014/ajot.39.6.386>.

Miazzoleni, S. et al., "Whole-body isometric force/torque measurements for functional assessment in neuro-rehabilitation: platform design, development and verification", Journal of Neuroengineering and Rehabilitation, Oct. 2009, vol. 6, No. 38, pp. 27-37 <DOI:10.1186/1743-0003-6-38>.

Moeslund,T. et al., "A survey of advances in vision-based human motion capture and analysis", Computer Vision and Image Understanding, Nov.-Dec. 2006, vol. 104, No. 2-3, pp. 90-126 <DOI:10.1016/j.cviu.2006.08.002>.

Morris, D. et al., "The reliability of the wolf motor function test for assessing upper extremity function after stroke", Archives of Physical Medicine and Rehabilitation, Jun. 2001, vol. 82, No. 6, pp. 750-755 <DOI:10.1053/ apmr.2001.23183>.

Nijland, R. et al., "A comparison of two validated tests for upper limb function after stroke: the Wolf Motor Function Test and the Action Research Arm Test", Journal of Rehabilitation Medicine, Jul. 2010, vol. 42, No. 7, pp. 694-696 <DOI:10.2340/16501977-0560>.

Oikonomidis, I. et al., "Efficient model-based 3D tracking of hand articulations using Kinect", British Machine Vision Conference, Aug. 29-Sep. 2, 2011, [available online Sep. 2011], pp. 1-11 <DOI:10.5244/C.25.101>.

(56) References Cited

OTHER PUBLICATIONS

Oikonomidis, I. et al., "Full dof tracking of a hand interacting with an object by modeling occlusions and physical aonstraints", 2011 IEEE International Conference on Computer Vision (Barcelona, Spain, Nov. 6-13, 2011), 2011 [Date Added to IEEE Xplore: Jan. 2012], pp. 2088-2095 <DOI:10.1109/ICCV.2011.6126483>.

Olesh, E. et al., "Automated assessment of upper extremity movement impairment due to stroke", PLoS One, Aug. 2014, vol. 9, No. 8, pp. 1-9 <DOI: 10.1371/journal.pone.0104487>.

Otten, P. et al., "A framework to automate assessment of upper-limb motor function impairment: A feasibility study", Sensors, Aug. 2015, vol. 15, No. 8, pp. 20097-20114 <DOI:10.3390/5150820097>.

Pang, M. et al., "A community-based upper-extremity group exercise program improves motor function and performance of functional activities in chronic stroke: a randomized controlled trial", Archives of Physical Medicine and Rehabilitation, Jan. 2006, vol. 87, No. 1, pp. 1-9 <DOI:10.1016/j.apmr.2005.08.113>.

Potter, K. et al., "Outcome Measures in Neurological Physical Therapy Practice: Part I. Making Sound Decisions", Journal of Neurologic Physical Therapy, Jun. 2011, vol. 35, No. 2, pp. 57-64 <DOI:10.1097/NPT.0b013e318219a51a>.

Santello, M. et al., "Gradual molding of the hand to object contours", Journal of Neurophysiology, Mar. 1998, vol. 19, No. 3, pp. 1307-1320 <DOI:10.1152/jn.1998.793.1307>.

Santello, M. et al., "Postural hand synergies for tool use", Journal of Neuroscience, Dec. 1998, vol. 18, No. 23, pp. 10105-10115 <DOI:10.1523/Jneurosci.18-23-10105.1998>.

Sears, E. et al., "Validity and Responsiveness of the Jebsen-Taylor Hand Function Test", Journal of Hand Surgery, Jan. 2010, [available online Dec. 2009], vol. 35, No. 1, pp. 30-37 <DOI.10.1016/j.jhsa.2009.09.008>.

Silaghi, M.-C. et al., "Local and Global Skeleton Fitting Techniques for Optical Motion Capture", International Workshop on Modelling and Motion Capture Techniques for Virtual Environments, Nov. 1998, pp. 26-40 <DOI:10.1007/3-540-49384-0_3>.

Simon, T. et al., "Hand Keypoint Detection in Single Images using Multiview Bootstrapping", arXiv, v1, submitted Apr. 25, 2017, 9 pages, https://arxiv.org/abs/1704.07809v1.

Simon, T. et al., "Hand Keypoint Detection in Single Images using Multiview Bootstrapping", IEEE Intenational conference on Computer Vision and Pattern Recognition (Honolulu, Hawaii, Jul. 21-26, 2017), 2017 [Date Added to IEEE Xplore: Nov. 2017], pp. 1145-1153 <DOI:10.1109/CVPR.2017A94>.

Sullivan, J. et al., "Outcome Measures for Individuals With Strokeo: Process and Recommendations From the American Physical Therapy Association Neurology Section Task Force", Physical Therapy, Oct. 2013, [available online May 2013], vol. 93, No. 10, pp. 1383—1396 <DOI:10.2522/ptj.20120492>.

Turaga, P. et aL, "Machine recognition of human activities: a survey", IEEE Transactions on Circuits and Systems for Video Technology, Nov. 2008, [available online Sep. 2008], vol. 18, No. 11, pp. 1473-1488 <DOI:10.1109/TCSVT.2008.2005594>.

Van Der Lee, J. et al., "Forced use of the upper extremity in chronic stroke patients", Stroke, Nov. 1999, vol. 30, No. 11, pp. 2369-2375 <DOI:10.1161/01.STR.30.112369>.

* cited by examiner

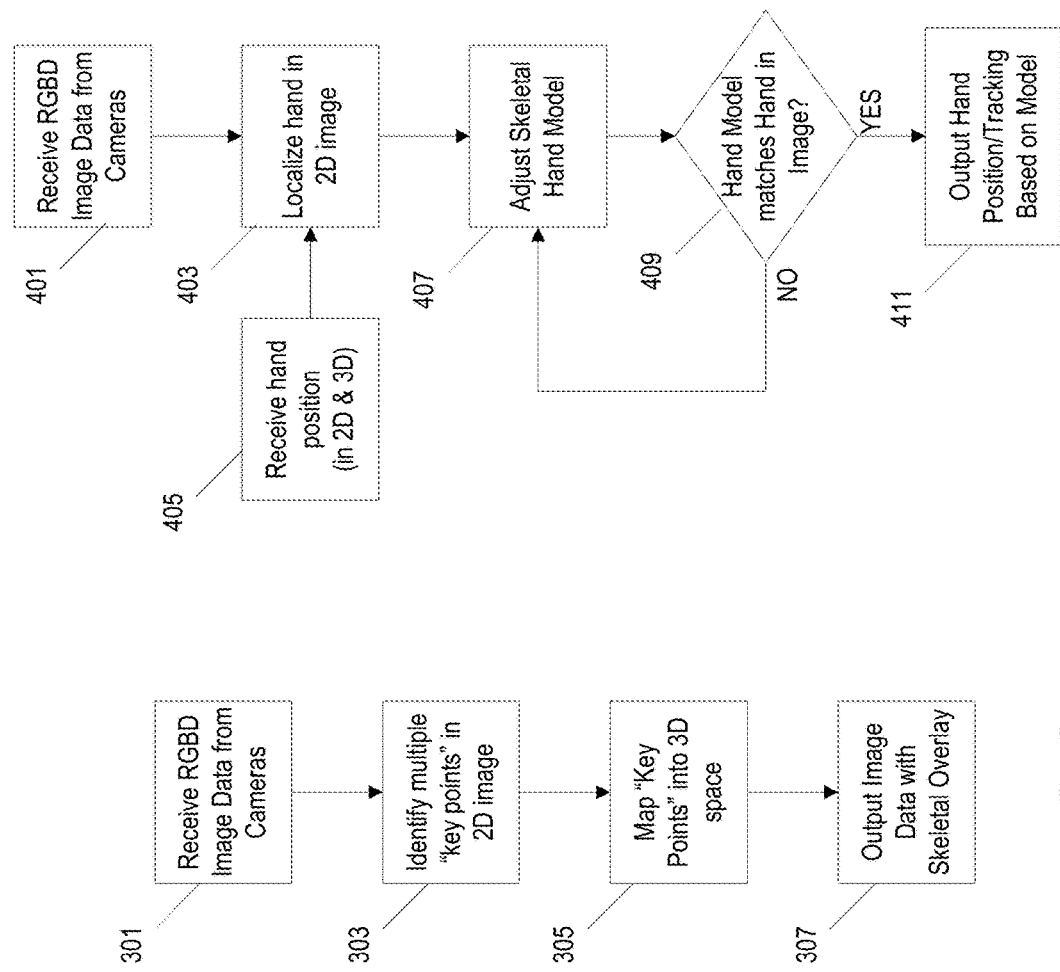
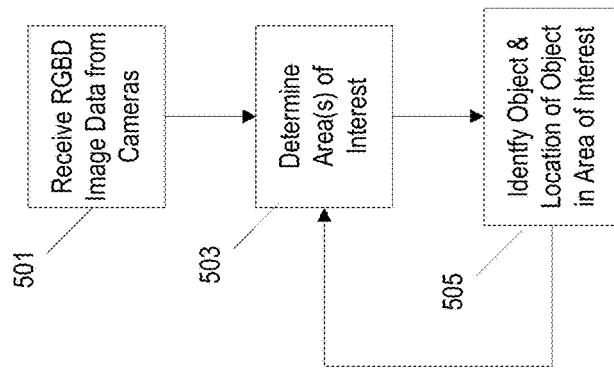
FIG. 5
FIG. 4
FIG. 3

COMPUTER-VISION-BASED CLINICAL ASSESSMENT OF UPPER EXTREMITY FUNCTION

RELATED APPLICATIONS

This application claims the benefit of U.S. Provisional Patent Application No. 62/596,652, filed Dec. 8, 2017, entitled "COMPUTER-VISION-BASED CLINICAL ASSESSMENT OF UPPER EXTREMITY FUNCTION," the entire contents of which are incorporated herein by reference.

BACKGROUND

This disclosure relates to systems and methods for quantitative assessment of human motion in patients with sensorimotor deficits.

Stroke is the leading cause of serious chronic physical disability in the United States, with 95% of stroke survivors exhibiting some Upper Extremity (UE) dysfunction and 30 to 66% with impaired ability to use the impaired arm. This has a substantial impact on the healthcare system and allocation of resources for an estimated 7.2 million affected Americans ≥20 years of age, and 610,000 new cases every year. Standardized routine Outcome Measures (OMs) of UE impairment are critical for driving clinical decisions about rehabilitation protocols and monitoring progression of sensorimotor deficits.

However, commonly-used clinical assessment of upper extremity (UE) function primarily relies on subjective evaluation of movement quality and/or time spent to complete a given task and is also often unable to provide sufficient evidence to assist therapists to develop and modify plan of care. This is because existing assessment tools rely on subjective grading of movement quality with a few discrete levels (e.g., Action Research Arm Test), and/or macroscopic metrics such as time-to-task completion (e.g., Nine-Hole Peg Test). Therefore, these OMs and the resulting metrics lack the sensitivity to detect subtle, but important, behavioral changes that might occur with progression of sensorimotor deficits and/or in response to medical treatment or to directly target and focus on specific functional deficits. This is especially problematic for the mildly impaired patients, as ceiling effects of existing assessment tools are frequently observed, which then results in little financial assistance by third party payers to support continued therapy.

SUMMARY

In some embodiments, the various systems and/or methods disclosed herein aim at providing objective and reliable measures of the quality and characteristics of human upper extremity movement during standard/routine clinical assessment. The unique design of the various systems and/or methods disclosed herein utilize computer vision algorithms that have been designed to track human motion without having to use wearable sensors or markers for motion tracking. The intervention can be used by clinicians to provide additional information relative to standard clinical assessment tools, thereby contributing to objective clinical evaluation of patients' sensorimotor function and clinical decision-making about medical intervention.

To assess the sensorimotor function of the upper extremity, a patient may be instructed to perform a series of tasks that are designed to cover a wide range of functional activities of daily life. Without the benefit of a machine-vision-based system, clinicians might visually observe the performance of these tasks, and subjectively assign a score to the movement quality. However, this type of subjective assessment may not provide enough sensitivity to detect subtle changes in the movements, and this limits their ability to provide key information that would guide clinicians to make effective clinical decisions. In various embodiments, the various systems and/or methods disclosed herein provide a measurement tool to provide additional clinical data during these standard assessments. Specifically, in certain embodiments, one non-limiting, example of a unique property of the various systems and/or methods disclosed herein is the technical integration and application of state-of-the-art computer vision algorithms.

In some embodiments, when clinicians administer clinical tests, one or two cameras are placed in the surrounding area to video-record the movement of the patient, as well as the interaction between the patient and the environment (e.g., grasping objects). For each frame of the video, spatial distribution of the colors are processed to extract information from the scene. This process integrates several novel algorithms that are responsible for computing the configuration of the human body (i.e., joint angles), as well as the position and orientation of the objects. The results of these computations allow the system to record subjects' and object's motion continuously in real time. After recording, the system computes offline a unique set of variables extracted from the motion of both patient and objects. Examples of these variables include movement smoothness and the temporal coupling of hand and arm motion. Data collected from patients is then compared with a database of normative data collected on healthy gender- and age-matched controls, and summarized in graphical and tabular formats for easy interpretation by clinicians.

In some implementations, the various systems and methods disclosed herein provide systems and methods for applying an objective movement quantification framework based on the integration of state-of-art computer vision (CV) technology and standard clinical practice. CV algorithms are configured to extract positions of upper limb segments (i.e., arm, forearm, hand, and fingers) and surrounding objects from video frames (i.e., images). This enables quantitative analyses of human UE activity directly from frames of video recordings of functional tasks (e.g., grasp and move objects). These functional tasks often require coordinated motion across many dimensions (i.e., joints and muscles) within the involved limb. Our pilot data indicate that our CV-based analyses are able to objectively capture the changes in multiple dimensions. Therefore, our framework promises an objective and more sensitive scale that can complement conventional clinical OMs, with minimal to no interference to existing clinical assessment procedure.

For example, both patients A and B might have moved 10 blocks in a Box and Block Test in one minute, but patient A could have had more difficulty opening and closing the fingers, whereas patient B might have been less able to properly lift his arm. Although these differences in individual joint movements for Box and Block Test may be captured by combining it with impairment scales, e.g., Fugl-Meyer Assessment (FMA), such evaluation would still be subjective as FMA is based on visual observation. Therefore, it is difficult to objectively determine the extent to which each joint contributes to the impaired functional outcome. In contrast, the framework provided by certain embodiments of the various the systems and methods disclosed herein accurately quantify the deficits in different components of UE functional performance, which leads to more precise clinical decisions driving the design of the rehabilitation protocol, i.e., focusing on intensive practice of hand versus shoulder movements. Furthermore, a more sensitive quantification system decreases ceiling effects, which provides better insights into the response to a given treatment. Lastly, the minimum cost and effort to implement our CV-based framework could allow automated assessment procedures and easy sharing of standardized OMs across rehabilitation clinicians.

Other aspects of the various systems and methods disclosed herein will become apparent by consideration of the detailed description and accompanying drawings.

BRIEF DESCRIPTION OF THE DRAWINGS

FIG. 3 is a flowchart of a method for mapping body movements in 3D space based on 2D image data using the system of FIG. 1.

FIG. 4 is a flowchart of a method for estimating a hand pose using the system of FIG. 1.

FIG. 5 is a flowchart of a method for tracking objects using the system of FIG. 1.

DETAILED DESCRIPTION

Before any embodiments of the various systems and/or methods disclosed herein are explained in detail, it is to be understood that such systems and methods are not limited in its application to the details of construction and the arrangement of components set forth in the following description or illustrated in the following drawings. The systems and methods are capable of other embodiments and of being practiced or of being carried out in various ways.

Quantitative assessment of human motion in patients with sensorimotor deficits has been a central topic for physical medicine and rehabilitation in the last decade. In some implementations, "robotics-based assessment" utilizes motorized mechanisms to measure patient's motor function in a highly constrained environment. However, a robotics-based approach may be very expensive and may use non-functional, artificial tasks that are difficult to interpret and associate with standard clinical OMs. In other implementations, body-worn sensors, such as inertial measurement units, optical markers, and data gloves, may be used to evaluate body motions. However, the number of sensors required would increase with the number of body segments and objects to be measured, making the setup time consuming, complex, and expensive. This is undesirable for clinical settings where patient's and physician's times are limited.

Figure 1:
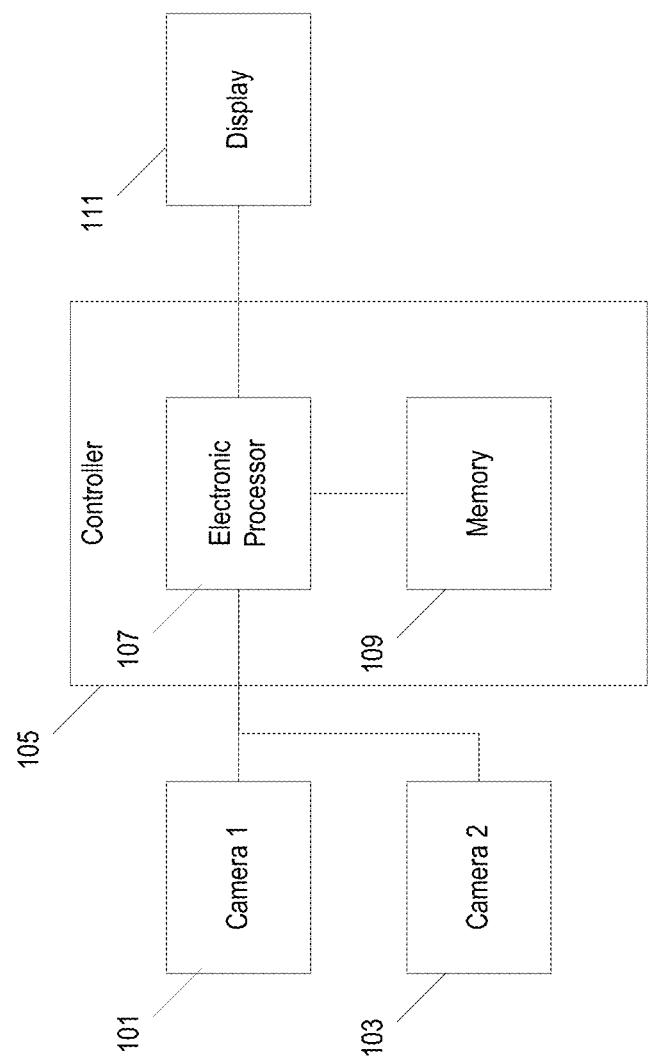
FIG. 1 is a block diagram of a control system for patient movement monitoring, evaluation, and imaging system according to one embodiment.

In still other implementations, markerless motion tracking is utilized using RGBD cameras—for example, the Microsoft Kinect. FIG. 1 illustrates one example of a system for evaluating human motion using markerless motion tracking. A plurality of cameras 101, 103 are communicatively coupled to a controller 105. In some implementations, the cameras 101, 103 include at least two RGBD cameras configured to capture both color and depth image frames (i.e., distance from camera) with 40×480 resolution at 30 frames per second. The controller 105 includes an electronic processor 107 and a computer-readable, non-transitory memory 109. The memory 109 stores instructions that are executed by the electronic processor 107 to provide the functionality of the controller 105 as discussed herein. The controller 105 is also coupled to a display 111 and is configured to output graphical output. For example, in some implementations, the system is configured to output on the display 111 one or more images captured by the one or more of the cameras 101, 103 with additional graphical items indicative of human anatomical structures and/or objects manipulated by the patient. In some implementations, the cameras 101, 103 are provided as part of the Microsoft Kinect and raw image data and/or processed image data is provided from the cameras 101, 103 to the controller 105.

Systems utilizing markerless motion tracking might utilize a skeletal tracking algorithm such as the Microsoft Kinect's own internal skeletal tracking algorithm. However, skeletal tracking alone would suffer from a number of limitations. For example, a skeletal tracking algorithm might not perform well if there are large objects (e.g., a table) between the camera 101/103 and subject (i.e., the patient and/or objects used in the test). It may also fail to provide information about finger joint movements and fail to track objects surrounding the hands of a patient. These limitations might prevent assessment of functional tasks that involve hand-object interactions, e.g. object grasping and manipulation. Therefore, the system illustrated in FIG. 1 is further configured to provide reliable kinematic tracking of additional UE body segments, while adding minimum to no financial burden or time to existing routine clinical OM tests. Another novel element of our approach is that it features object tracking in the proximity of UE, which allows estimation of hand-object interactions in functional tasks.

In the examples described below, a patient is instructed to perform one or more of three clinical tests includes the Action Research Arm Test (ARAT), the Box and Block Test (BBT), and the Nine-Hole Peg Test (NHPT). These tests were selected based on the following criteria: 1) they are based on functional tasks that resemble activities of daily living; 2) the tests should be commonly used by the clinical community; 3) combined, the tests should provide complementary OMs ranging from gross to fine UE motor function. However, in some implementations, the systems and methods described herein can be configured to monitor other clinical functional tests (e.g., Jebsen hand function test, Wolf Motor Function Test) in addition to or instead of the ARAT, BBT, and NHPT as discussed herein. Furthermore, the inventive systems and methods can be adapted to use other clinical tasks to evaluate more specific objectives and may be further adapted for automated assessment of UE impairment.

The Action Research Arm Test (ARAT) is designed to assess coordination and dexterity using functional tasks. Nineteen different items are used in this assessment and the 19 items are divided into four sub-groups relating to different aspects of upper extremity movement: Grasp, Grip, Pinch, and Gross arm movement. The assessment requires the patient to reach towards an object, grasp the object, transport the object to another location, and replace objects of different sizes and shapes. ARAT has both within and across sub-group difficulty levels, which allows skipping tasks if ceiling or floor effects are observed in tasks with the least or most difficulty level. Each item is scored as follows: 0—cannot perform task; 1—partial perform; 2—complete, but slow; 3—complete. Therefore the maximum score is 57.

The Box & Block Test (BBT) is used to measure functional manual dexterity. This test requires the patient to transport as many 2.5 cm square blocks as possible, one by one, from one compartment of a box to another compartment of equal size (25.4 cm sides, 7.5 cm height). A partition (15.2 cm height) separates the two compartments. Therefore, a successful transport of a block requires subjects to grab a block, lift their hands and move their fingers over the partition, and then release the block. The score is computed as the total number of blocks moved within 60 seconds.

The Nine-Hole Peg Test (NHPT) is designed to assess finger dexterity. This task has the highest dexterity requirement among all selected tests. Subjects are asked to take pegs (0.64 cm in diameter, 3.2 cm long) from a shallow dish, one by one, and place them into the holes (1.3 cm deep, 3.2 cm apart) on a board, as quickly as possible. After inserting all nine pegs, subjects have to remove them from the holes, one by one, and replace them back into the container. The only score is computed as the total time taken to complete the task.

Figure 2:
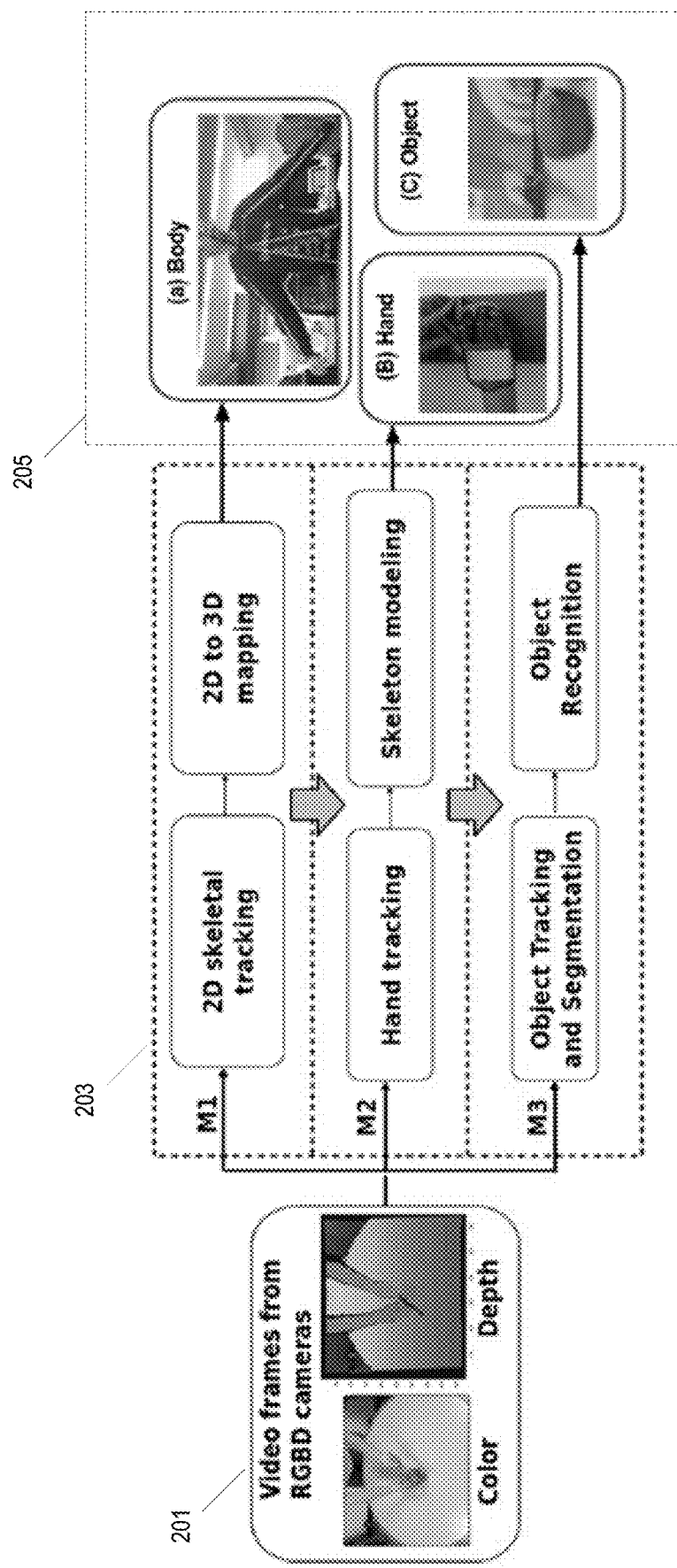
FIG. 2 is a flowchart of a method for tracking human actions in clinical assessment tests and for displaying graphic-based imaging indicative of patient-action characteristics using the computer vision system of FIG. 1.

FIG. 2 illustrates a method for capturing and processing movement data using the system of FIG. 1 while the patient performs one or more clinical assessment tasks. As color and depth image data is captured by the cameras (step 201), the controller processes the image data (step 203) to perform upper body skeleton tracking (M1), hand posture estimation (M2), and object tracking (M3). The system then uses data acquired by processing the images to calculate metrics and/or display versions of the captured images with overlaid annotations (for example, illustrating an approximation of skeletal body movements (a), color coding identifying different parts of a hand (b), and highlighting identified objects (c)) (step 205).

As described in further detail below, upper body skeleton tracking (M1) analyzes the captured images to identify & track skeletal movements of the body and to map the position/movement of certain body points in 3D space based on the captured 2D image data. The hand posture estimation (M2) tracks movements of the hand and performs a best fit analysis between the captured image data of the hand and an estimated corresponding position of a 3D skeleton model of the hand. Furthermore, the identified location of the hand in the upper body skeleton tracking (M1) can be used as an input to the hand posture estimation (M2) to reduce computational complexity. Object tracking (M3) is performed by using object recognition techniques to identify and locate objections of known size and dimensions in the captured image data (e.g., blocks or pegs used in the assessments).

FIG. 3 illustrates an example of a method for performing the upper body skeleton tracking (M1) of FIG. 2. This method tracks the joint motion of upper extremity (UE) movement using a set of algorithms for real-time multi-person key-point detection in color images. A series of RGBD images are received from the camera(s) 101, 103 (step 301) and the controller 105 applies a nonparametric representation to learn to associate body parts with the appearances of individuals in each image frame. By applying the nonparametric representation, the controller 105 is able to detect multiple different specific "key points" on a human body in the captured images (step 303). In some implementations, the system is capable of reliable detection of up to 18 key points on one human body. These key points represent important body landmarks, i.e., joint centers, which allow construction of UE skeletons. In some implementations, the system is configured to identify key points in the 2D image data corresponding to the shoulders, elbows, wrists, neck, head, and hands of the patient.

After the key points are detected in the image data, the controller 105 maps the key points to three-dimensional (3D) space (step 305) based, for example, on the depth image using a geometry-based technique and/or triangulation using an identified location of the same key point in the 2D image data captured by multiple different cameras. By detecting the position of each "key point" in multiple different images, the controller 105 is able to track movements of particular body parts over time. Furthermore, by monitoring movements of one key point relative to another, the controller 105 is able to monitor movements indicative of joint kinematics. For example, by monitoring a movements of a key point corresponding to the wrist of a patient relative to a key point corresponding to the elbow of the patient, the controller 105 is able to monitor and quantify kinematics (e.g., range of motion) of the elbow joint.

Finally, in some implementations, the controller 105 may be configured to generate a stream of output images to the display where the identified locations of multiple key points are overlaid onto images captured by the camera(s) (step 307). In some such, implementations, as illustrated in FIG. 2 ("(a) Body"), the controller 105 is also configured to display overlaid lines connecting key points that are skeletally coupled to each other (e.g., a line connecting the elbow point to the wrist point).

One of the unique features of the system is the ability to track hand posture when subjects are interacting with objects (see, e.g., "(B) Hand" in FIG. 2). FIG. 4 illustrates one example of a method for determining and tracking hand posture. The controller 105 receives image data from the camera(s) 101, 103 (e.g., the same image data provide as an input in the method of FIG. 3) (step 401) and processes the image data to localize a hand in the captured image (step 403). As discussed above, in some implementations, the "hand" is one of the key points identified by the controller 105 in the body motion tracking method of FIG. 3. Accordingly, in some implementations, the controller 105 may be configured to localize the hand in the image data (step 403) based in part on an identification of the hand in the 2D image and/or in 3D space based on hand position information determined by the body motion tracking (step 405).

In some implementations, the system is configured to identify the location of a hand by identifying and analyzing the largest contour present in the frame. For example, if the cameras are positioned/configured to capture an entire arm of the patient, the largest contour in the image frame may correspond to the patient's arm and the hand can be located by following the contour to its distal end. Conversely, in situations and implementations where the camera is configured to capture only a close-up image of the hand, the largest contour in the image may instead correspond to an edge of the hand itself.

Furthermore in some implementations, the controller 105 may be configured to isolate pixels in the captured image data corresponding to the hand by applying a generic skin color model that is robust to skin color differences. The color model can be applied before determining a general location of the hand (i.e., to isolate all pixels corresponding to skin) or after the general location of the hand is determined (i.e., to separate the hand from the background). In some implementations, the controller 105 may be configured to output an image of the hand to the display including a color-coded overlay that identifies the location of the hand as shown in the example of FIG. 2 (i.e., "(B) Hand").

Once the patient's hand is identified and isolated in the captured image data, the controller 105 accesses one or more fine grain skeletal models of a hand from the memory. The skeletal hand model can, in some implementations, be generated based specifically on the size and shape of a particular patients hand while, in other implementations, the skeletal hand model is a generic model. The controller 105 is configured to adjust a size and orientation of the hand model and positions of individual joints in the hand (step 407) until the hand model matches the hand as pictured in a particular frame of the captured image data (step 409). In this way, the controller 105 is configured to estimate the full articulation of a hand (26 degrees of freedom redundantly encoded in 27 parameters) involved in unconstrained motion through a matching mechanism between simulated image of an estimated hand model and an input-captured image of the patient's actual hand. Through this mechanism, the system can also handle occlusions caused by a human hand manipulating objects. By applying this hand posture estimation technique to multiple successive image frames captured by the camera(s), the controller 105 is able to track small-scale hand movements as the patient performs the tasks of the assessment procedure.

FIG. 5 illustrates an example of a method that may be used in some implementations for the object tracking (M3). This method combines segmentation and tracking to estimate the position and motion of the objects used in some of the selected assessment tests. The controller 105 again receives the image data from the camera(s) (step 501) and a stochastic tracking algorithm generates areas of interest based on object appearance known a priori (step 503). The "a priori" information that is used to determine areas of interest can include, for example, a location of the same object detected in a previous image frame and/or a known starting location determined by the design of the assessment equipment (e.g., an initial "area of interest" in the Nine-Hole Peg Test (NHPT) may include the shallow dish in which the pegs are initial located). The tracked objects are then automatically recognized by searching each "area of interest" against a database including all standard objects involved in these clinical tests, for example, by comparing associated color, texture, and shape features (step 505). Then color, texture, and shape information surrounding the area of interest are used for the segmentation algorithm to update object appearance models for the next time step (e.g., to be used by the controller 105 in order to define an area of interest and/or detect a location/orientation of an object in a subsequent image frame captured by the camera(s)). This design enables robust tracking of multiple objects despite of potential partial occlusion (see, e.g., "(C) Object" in FIG. 2).

While each of the three recognition methods described in reference to FIGS. 3, 4, and 5 are robust and reliable on a single camera, their combination across two cameras (or more) allows fusion of complementary information from multiple algorithms which further improves the overall performance. As noted above, the output of the "skeletal module" (FIG. 3) helps the "hand module" (FIG. 4) to localize potential areas of hands and the combination of "hand module" (FIG. 4) with the "object module" (FIG. 5) can be used to identify action components to complete functional tasks, such as 'grasp', 'move', and 'drop'. As discussed in further detail below, all the tracked signals can be used to extract behavioral features while the patient performs an assessment task.

Using the skeletal model estimated from CV algorithms (e.g., FIG. 3), the controller 105 is configured to compute kinematic variables that describe the motion. For the arm, the controller 105 may be configured to measure movement/positions relating to the following 9 joints: wrist flexion/extension, wrist supination/pronation, elbow flexion/extension, shoulder flexion/extension, shoulder abduction/adduction, shoulder internal/external rotation, and scapular elevation.

Figure 6:
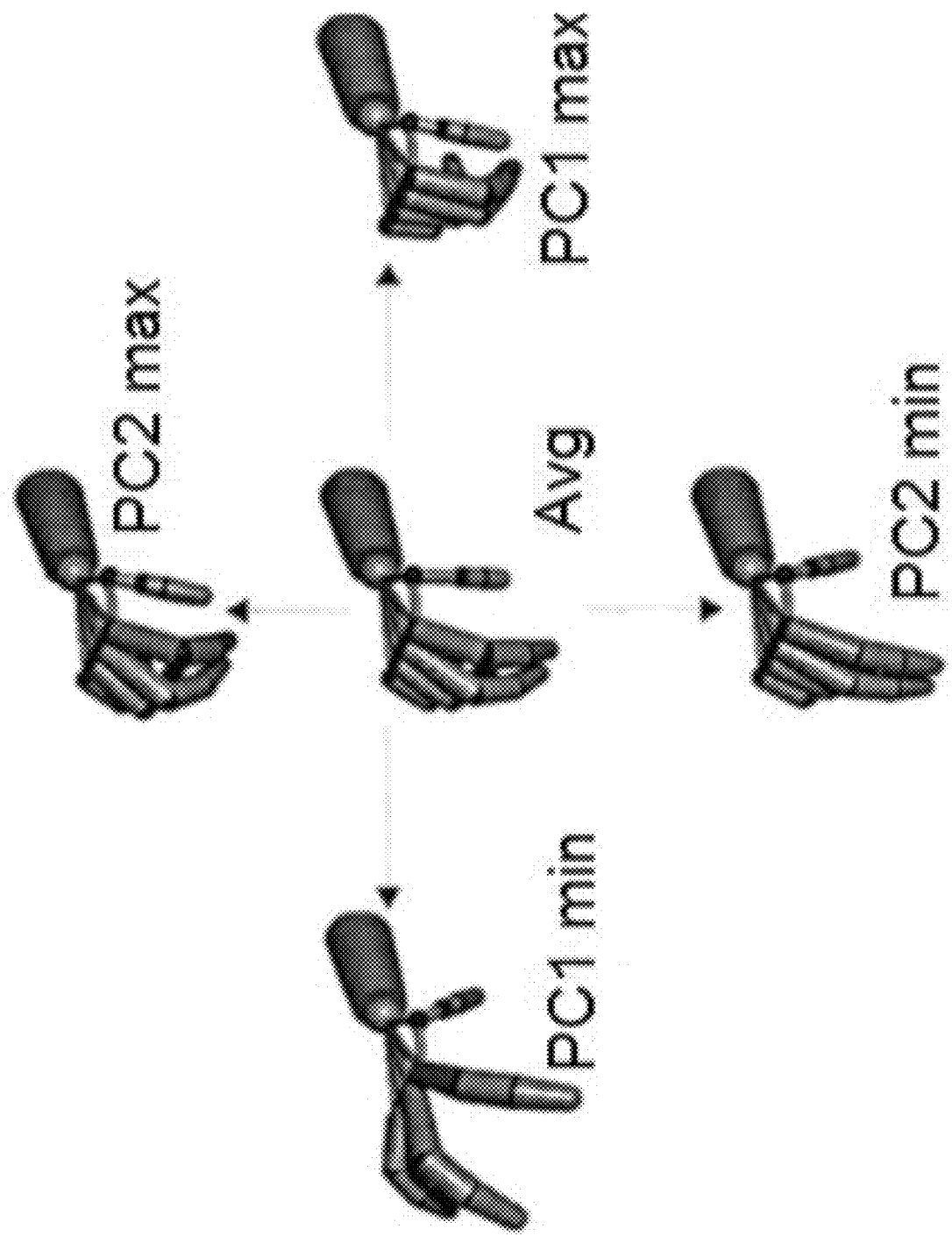
FIG. 6 is a schematic example of movement characteristics performed by a patient and evaluated/imaged using the method of FIG. 2.

The systems and methods described herein are also configured to track finger movements. However, the fingers consist of many joints and, in some implementations, it might be impractical to examine movements of each individual joint. Instead, in some implementations, the system is configured to focus on finger coordination patterns. Finger motions associated with grasping of a wide range of common objects can be approximated by a few synergies, i.e., covariation patterns of finger joints. FIG. 6 illustrates an example of two finger motion "synergies" that the controller 105 may be configured to monitor. The first synergy (PC1) represents an approximately equal motion of all joints in the hand and may be indicative of the hand opening and closing. "PC1 min" (as illustrated in FIG. 6) represents all of the finger joints at their smallest measured bending (e.g., the patient's hand is opened) and, in contrast, "PC1 max" represents all of the finger joints at their largest collective bending (e.g., the patient's hand in a "closed" position). The second synergy (PC2) represents selective coordinated motion of the thumb, index, and middle fingers and may be indicative of the patient gripping and releasing an object. "PC2 max" (as illustrated in FIG. 6) represents the joints of the three fingers at their largest observed bending (e.g., when the patient's hand has gripped an object) and, in contrast, "PC2 min" represents the joints of the same three fingers at their lowest observed bending (e.g., when the patient's hand has released an object). "Avg" as illustrated in FIG. 6 represents the joints of all of the patient's fingers at their relatively average bending position (e.g., the patient's hand at rest). These synergies can be identified using principal component analysis (PCA), and the first two synergies (i.e., PCs explaining >80% total variance in PCA) are highly consistent across subjects. In some implementations, the system is configured to use movement along these two joint covariation patterns to extract finger synergies, thereby reducing dimensionality.

Figure 7A:
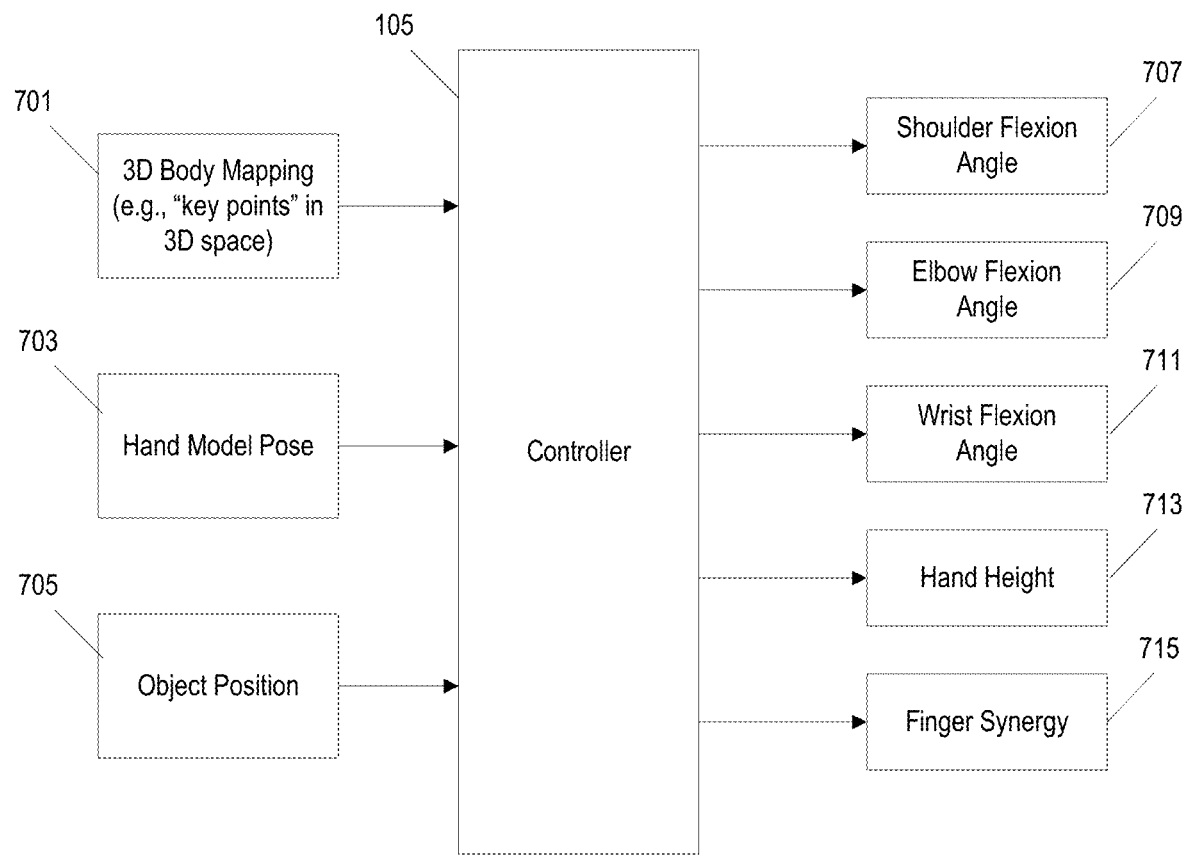
FIGS. 7A and 7B are flowcharts indicating various metrics that are determined by the system of FIG. 1 based on captured image data.
Figure 7B:
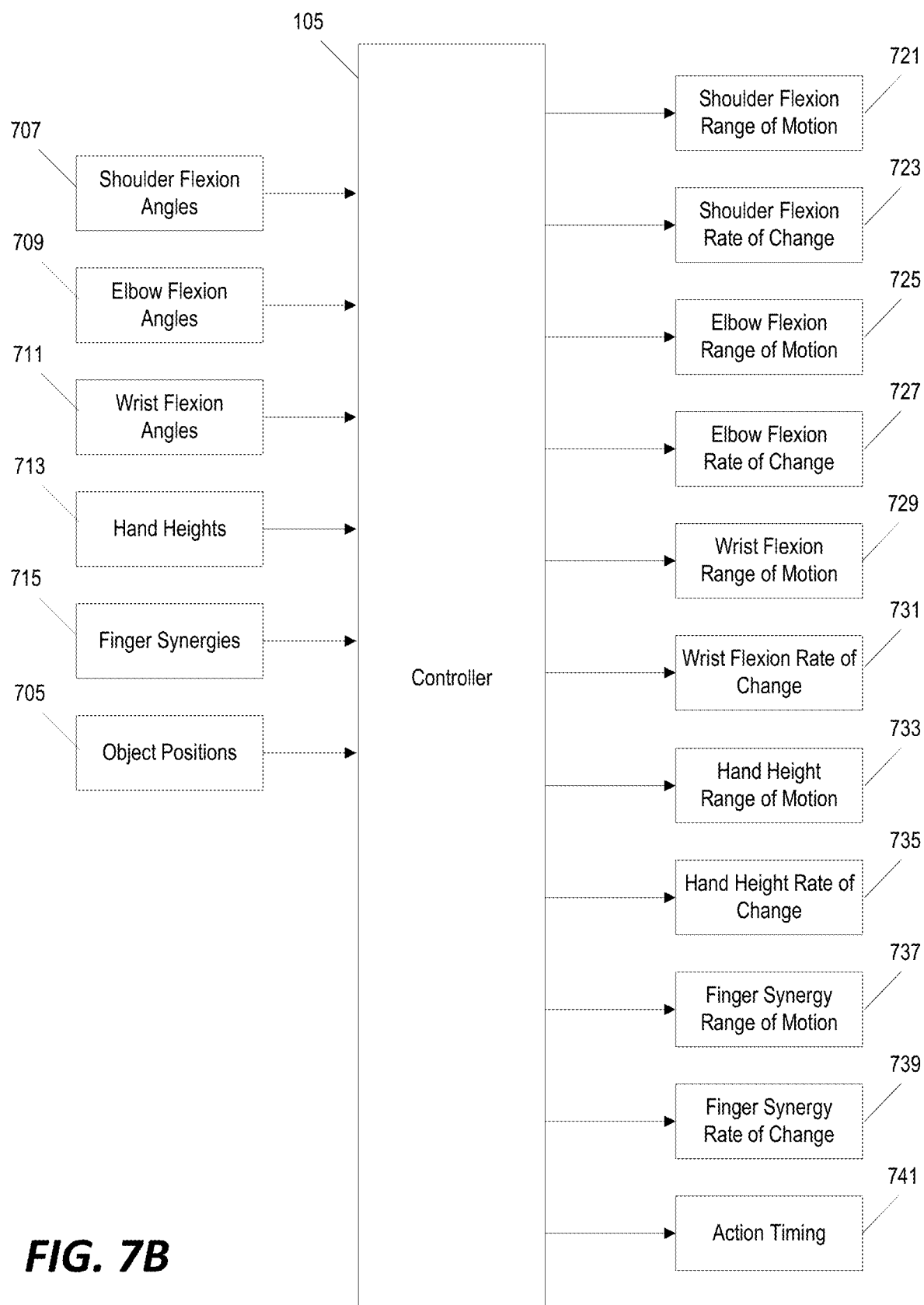

FIGS. 7A and 7B illustrate examples of some of the quantitative metrics that can be determined by the controller 105 based on the output of the 3D body mapping 701 (from FIG. 3), the Hand Model Pose 703 (FIG. 4), and the Object Position 705 (FIG. 5). For example, the controller 105 may be configured to determine a shoulder flexion angle 707 based on the "key points" identified in a single 2D image corresponding to the patient's neck, shoulder, and elbow by defining a first line in 3D space from the neck point to the shoulder point and a second line in 3D space from the shoulder point to the elbow point and determining an angle between the first line and the second line. Similarly, the controller 105 may be configured to determine an elbow flexion angle 709 based on the key points identified in the image corresponding to the shoulder, the elbow, and the wrist. The controller 105 may be further configured to determine a wrist flexion angle 711 based on key points identified in the image corresponding to the elbow, the wrist, and the hand of the patient. The controller 105 may also be configured to determine a hand height based on the key point corresponding to the hand from the 3D body mapping 701 and/or information from the hand model pose 703. Also, as discussed above in reference to FIG. 6, the controller 105 may also be configured to quantify a degree of finger synergy 715 from the hand model pose 703 based, for example, on the joint angles of one or more particular fingers of the hand.

The controller 105 may be configured to calculate metrics such as, for example, those illustrated in FIG. 7A at multiple different times (e.g., based on individual image frames captured by the camera(s) at each of a plurality of different times). Furthermore, the controller 105 may be further configured to determine additional metrics by compiling values of each metrics over a period of time while the patient performs the assessment task. For example, based on a series of shoulder flexion angles 707, the controller 105 can determine a shoulder flexion range of motion 721 (e.g., a difference between the maximum observed should flexion angle and the minimum observed shoulder flexion angle) as well as a shoulder flexion rate of change 723 (e.g., a calculated average rate of change of the shoulder flexion angle 707 over time). Similarly, based on a series of elbow flexion angles 709, the controller 105 can determine an elbow flexion range of motion 725 and an elbow flexion rate of change 727; based on a series of wrist flexion angles 711, the controller 105 can determine a wrist flexion angle range of motion 729 and a wrist flexion angle rate of change 731; based on a series of hand heights 713, the controller 105 can determine a hand height range of motion 733 and a hand height rate of change 735; and based on a series of finger synergies 715, the controller 105 can determine a finger synergy range of motion 737 and a finger synergy rate of change 739.

In some implementations, the controller 105 is also configured to compute task-specific features based on the timing of particular actions in tasks involving objects, which can be used to identify the source of slowness in these functional tasks (i.e., action timing 741). For example, the controller 105 may be configured to identify the time at which an object is gripped (i.e., picked up) and the time at which an object is dropped. For tasks where the patient is asked to move an object from one location to another, the controller 105 may also be configured to calculate an amount of time from the beginning of movement (i.e., hand moves from a position above the original location of an object) to the end of the movement (i.e., hand stops before dropping/releasing the object). In some implementations, the controller 105 is configured to determine task specific action timing based on object positions 705 (e.g., as determined in the method of FIG. 5), body mapping 701 (e.g., as determined in the method of FIG. 3), and/or hand model pose 703 (e.g., as determined in the method of FIG. 4). For example, the controller 105 may be configured to detect the time at which an object is gripped by the patient based by detecting a time at which the position of the object begins to move and/or a time at which the finger synergy reaches a maximum or threshold value. The controller 105 may also be configured to determine the timing associated with movement of an object from one location to another based on the time at which an object begins moving while gripped in the patient's hand to the time at which the object moves relative to the patient's hand (i.e., when the patient's hand releases/drops the object). As discussed in the examples below, in some implementations, different specific "action timings" can be defined and tracked depending on the particular assessment task being performed by the patient.

Action components timing for ARAT. As discussed above, three of the four sub-groups of test items in the Action Research Arm Test (ARAT) involve interaction with objects (Grasp, Grip, and Pinch). These items require the patient to perform the following action components on each object to complete the task: reach, grasp, move, place, and return. These action components can be identified based on the position and velocity of the hand in relation to the target objects/regions. In some implementations, the controller 105 may be configured to compute the averaged time of these five action components within each of the three sub-groups.

Action components' timing for BBT. If at least one block can be moved across the partition, the controller 105 can segment the action components of the Box & Block Test (BBT) based on the interaction between the hand, blocks, and the box. Specifically, in some implementations, the controller 105 is configured to compute the time for a subject to grasp and drop each block, as well as the move time between grasp and drop. If multiple blocks are moved, each measure is averaged by the controller 105 by the number of blocks.

Action components timing for NHPT. The controller 105, in some implementations, may be configured to segment the total time based on the interaction between the hand, the peg, and the board similar to the BBT described above. The time for a subject to pick up and insert each peg, and the time between the two actions, are computed and averaged by the controller 105.

Figure 8:
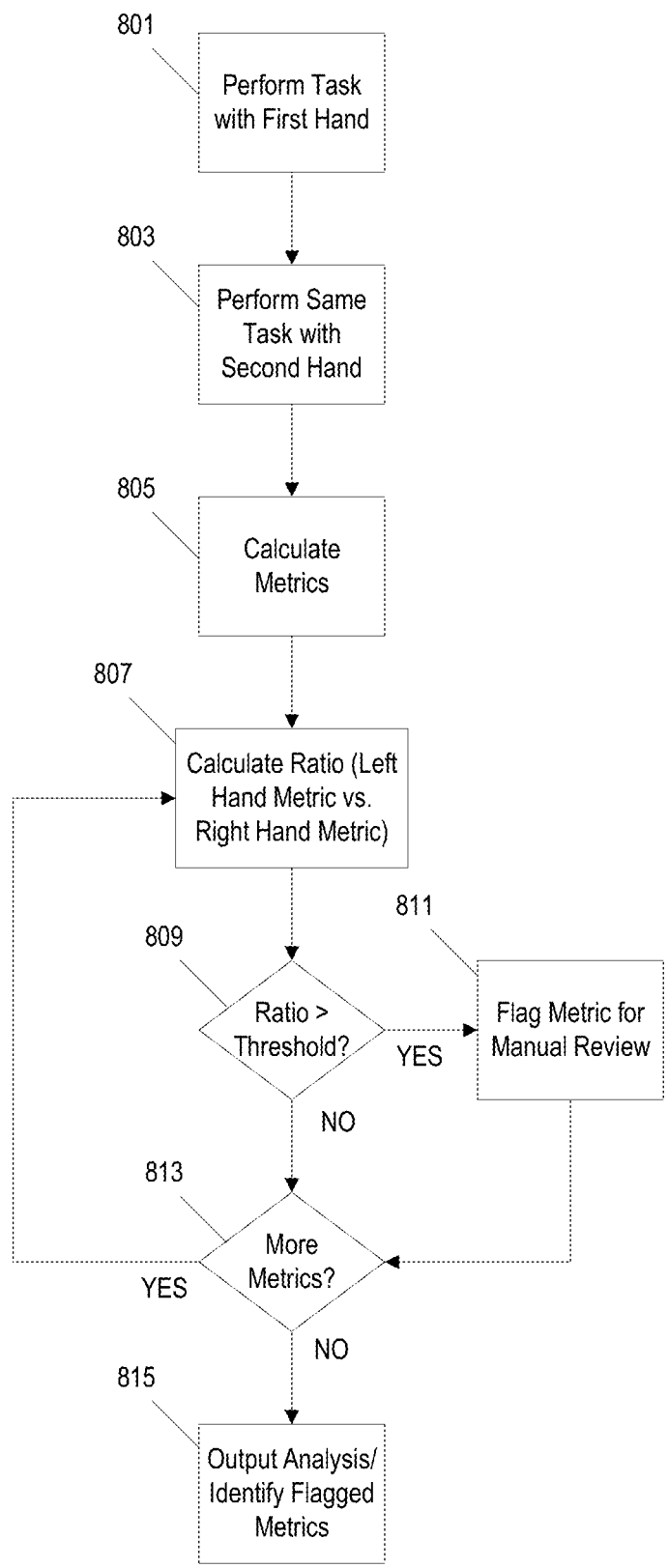
FIG. 8 is a flowchart of a method for identifying specific aspects of upper extremity motor impairment in a patient using the system of FIG. 1.

In some implementations, the controller 105 may be configured to provide further information (e.g., regarding the source or cause of slow performance or a particular joint/movement that exhibits significant impairment) based on an analysis of metrics determined by the controller 105 based on the captured image data. FIG. 8 illustrates one example in which a patient that exhibits impairment on only one side of the upper body is instructed to separately perform the same assessment tasks with each arm. First, the patient performs the assessment tasks with a first hand (step 801) and then the patient performs the same assessment tasks with the other hand (step 803) while the system captures image data. The image data is processed by the controller 105 to calculate various metrics observed for the tasks performed using the first hand and to calculate the same metrics observed for the tasks performed using the second hand (step 805). For example, the controller 105 may be configured to calculate a range of motion for the patient's should joint, elbow joint, wrist joint, hand height, and finger synergies for each hand. Corresponding metrics for each arm are then compared by the controller 105 to calculate a ratio (step 807). This provides a measurement/comparison of normalized range of motion impairment as a ratio between the impaired and contralateral sides (e.g., a ratio<1 indicates a smaller range of motion). Similarly, comparing the detecting timing features for the first hand to the same timing features for the second hand enables a quantification of normalized impairment in each action components as the ratio between the impaired and contralateral sides (e.g., a ratio>1 indicates a longer time required to perform the same action).

If the ratio of a particular metric exceeds a threshold (step 809), the controller 105 may be configured to flag the metric for further manual review (step 811). This process is repeated for all metrics calculated by the controller (step 813). In some implementations, the controller 105 utilizes a static ratio threshold for all metrics. In other implementations, different ratio thresholds can be defined (either manually, statically, or experimentally) for each different metric. In still other implementations, a dynamic ratio threshold is used in order to identify aspects of the patient's upper extremity movement that exhibit the most significant impairment. After all metrics for the first arm are compared to the corresponding metrics for the second arm, the controller 105 provides an output summary of the analysis (step 815). This output may help the medical professional identify certain aspects of the patient's upper extremity motion that exhibit the most significant impairment. It might also be utilized by a medical professional in determining an appropriate physical therapy/treatment that is targeted towards addressing a particular aspect of upper extremity motor impairment. Accordingly, in some implementations, the controller 105 may be further configured to identify and display a recommended treatment plan based on one or more of the metrics and/or ratios as calculated by the controller 105 based on the captured image data.

FIG. 8 illustrates just one example of how the image processing mechanisms might be used to identify, quantify, and evaluate various different aspects of upper extremity motor impairment. Other mechanisms are also possible. For example, metrics calculated based on image data captured while a patient performs the assessment tasks may be compared to normative data collected on healthy individuals. In some implementations, the normative data is specifically tailored to individuals using gender- and age-matched controls. Furthermore, the output of the analysis can be displayed in various different formats including, for example, graphical and/or tabular formats for easy interpretation by clinicians.

In one particular example, the system of FIG. 1 was used to collect data on two stroke patients. Patient MR30 was a 28-year old male who suffered moderate left hemisphere ischemic stroke. At the time of testing, he was 6 months post stroke and scored 35/66 in FMA UE (subscores: Shoulder and Arm 24/36, Wrist 3/10, Hand 6/14, Coordination 2/6). Additionally, he had no touch and location sense in his upper right arm according to FMA sensation test.

Figure 9A:
FIG. 9A is a screen shot of body skeletal tracking and imaging output on a display of the system of FIG. 1.
Figure 9B:
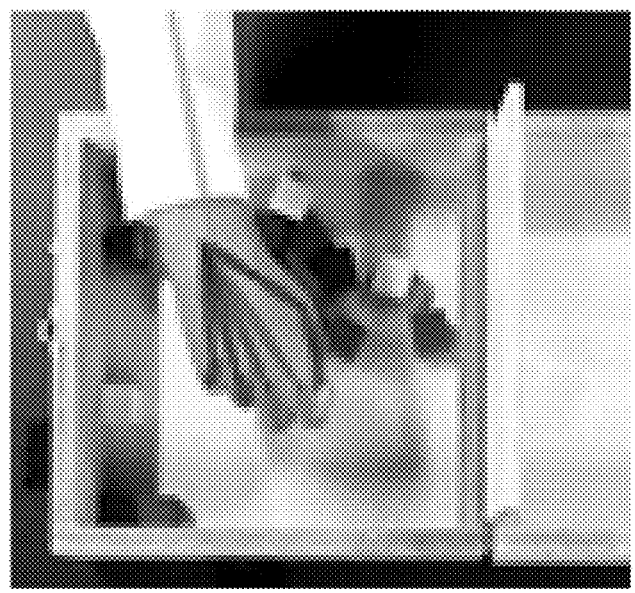
FIG. 9B is a screen shot of hand skeletal tracking and imaging output on the display of the system of FIG. 1.
Figure 9D:
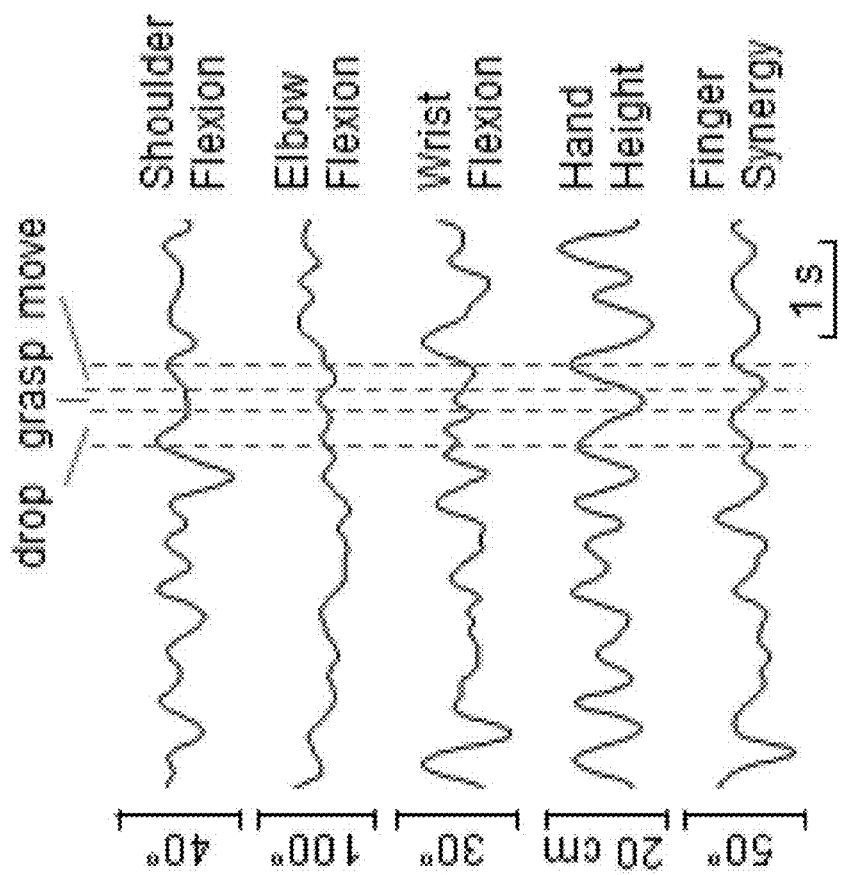
FIG. 9D is a graph of estimated kinematic variables as determined and displayed by the system of FIG. 1 for the other arm of the same patient as in FIG. 9C without impaired extremity function.
Figure 9C:
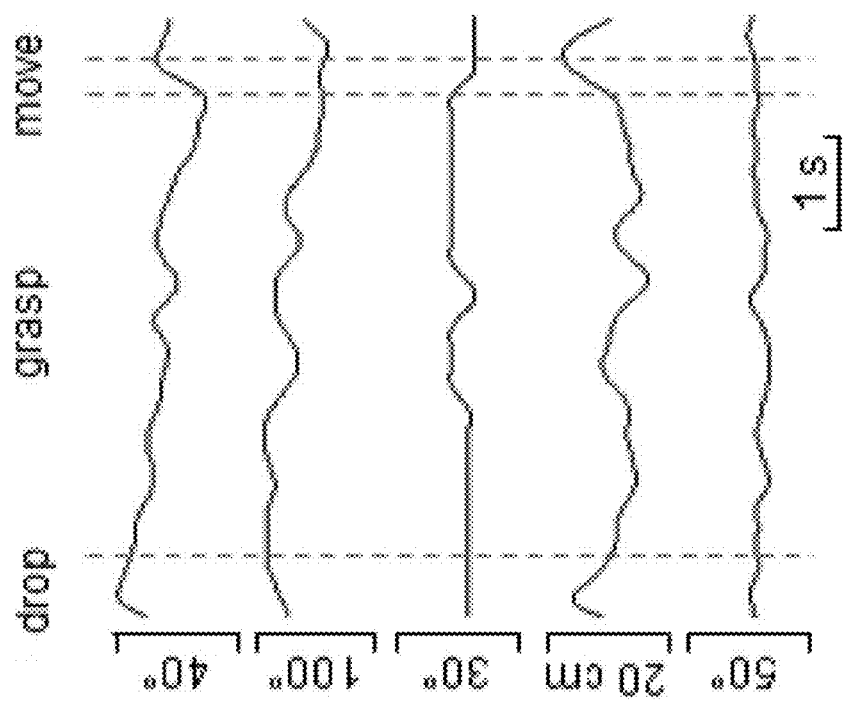
FIG. 9C is a graph of estimated kinematic variables as determined and displayed by the system of FIG. 1 of an arm of a patient with impaired extremity function.

As illustrated in FIGS. 9A and 9B, the system tracked his movement with side and top view cameras during BBT and he scored 3 and 68 for impaired and contralateral sides, respectively. This difference in speed can be clearly observed in the kinematic variables extracted from the CV system as illustrated in the graphs of FIGS. 9C and 9D. Within the same selected time period, the impaired side only transported one block successfully (FIG. 9C), whereas the contralateral side transported multiple blocks (FIG. 9D; only one block transport is labeled with action components). To further understand the cause of his impairment, the inventors compared the RoM over 60 seconds between two sides by computing the ratio as described above. The inventors found that his shoulder and elbow RoM for flexion/extension in the impaired side are similar to the contralateral side (ratios: 1.03 and 0.98, respectively). Similar scores were also found in most other limb joints (not shown due to space limit). However the RoMs for wrist flexion/extension and first finger synergy were severely limited (ratios: 0.27 and 0.28, respectively). Additionally, analysis of timing of action components revealed that time to grasp was much longer in the impaired side (ratio 21.6). Overall, these data suggest that our system can identify specific motor deficits that contribute the most to the BBT functional outcome score. This information complements the insights provided by clinical assessment tests to drive patient-specific clinical decisions. Specifically, the physical therapist may need to prioritize rehabilitation protocols that focus on motion and strength of his impaired hand and wrist to best improve overall functional performance within limited time during his visit in the clinic.

A second patient (MR33; 65-year old, female, 2 years post stroke, 66/66 in FMA UE) with a mild left hemisphere ischemic stroke was also tested. Her BBT scores were 62 and 73 for impaired and contraleral sides, respectively. Most of her behavioral features were comparable across the two sides. Importantly, however, our method identified the cause of the worse score for the impaired side as longer time to grasp than the contralateral side (ratio: 1.18). This could suggest mild dyspraxia (i.e., impaired motor coordination) in her impaired hand.

In some implementations, the accuracy of the CV algorithms is validated and optimized in healthy subjects by comparing results obtained from CV algorithms to 'ground truth' results obtained from standard research-grade Mocap systems and calculating the same behavioral features described above. Specifically, hand kinematics are measured by a pair of wireless data gloves (Cyberglove III), each sampling 15 finger joints and 2 wrist joint angles with 1° resolution at 100 Hz. The gloves have all fingertips exposed to allow tactile sensing. Both arms/hands and upper torso are tracked as a rigid-segment skeletal system with active marker sets (3 markers per segment, total 24 markers; 1-mm resolution, 120 Hz; Impulse, PhaseSpace Inc.). Appropriate calibration procedures are performed to ensure accurate estimation of segment length, as well as center and axis of rotation for shoulders, elbows, and wrists. Model-based skeletal tracking are implemented by the system for estimating subjects' RoM features during clinical assessment tests. Note that it is impossible for Mocap systems to track small objects (e.g., tubes, blocks, pegs) used in these tasks without interfering with task execution. Therefore, two experimenters will label the start and end of action components using videos recorded in synchronization with the Mocap systems. The timing features extracted from these labels are averaged across two experimenters and used as 'ground truth' to validate results from CV algorithms, as routinely done in the field of computer vision.

In one particular example, thirty-six healthy subjects with no history of neurological disorders or musculoskeletal injuries are recruited. Handedness is assessed through the Edinburgh Handedness Inventory. The experimental setup (e.g., chair and table) mimics the clinical setting where the same assessment tests are performed following standard procedures. Subjects are randomly assigned to one of three groups (n=12 per group), which are distinguished by the RGBD camera spatial configurations. All camera locations are in a plane parallel to subject's frontal plane, facing the center of the table at a distance of 1.5 m. C1 consists of one camera perpendicular and one camera parallel to the table (i.e., side and top views in FIGS. 4A and 4B). C2 consists of two cameras placed at 75° angle from the table, whereas C3 consists of two cameras at 45° angle from the table. The goal is to determine the best pair of cameras configuration with highest accuracy and reliability. Note that it may be impractical to have all six positions in one configuration because this creates interference among cameras. All subjects follow the same experimental procedure which consists of one Mocap session and one CV session. For both sessions, subjects perform the three clinical tests in the same order: ARAT, BBT, and NHPT. Within each test, subjects use their right side first, followed by left side. Subjects wear the gloves and marker sets during the Mocap sessions, but not in the CV sessions. The subjects take 2- and 5-minute breaks between tests and sessions, respectively.

After the CV algorithms are validated, the system can be adapted to quantify UE motor impairment in stroke patients. The inventors plan to record data from at least 50 patients within 18 months. Briefly, the inventors will recruit 25 patients with FMA scores ranging between 27 and 57 (i.e., moderate) and 25 patients with FMA scores ranging between 58 and 66 (i.e., mild). Only patients who are between one week and six months post stroke will be recruited because quantitative evaluation of OM is particularly critical in this time period during which patients undergo intensive functional rehabilitation treatment. Each patient will be tested as part of their standard clinical evaluations, with the only exception that their activities will also be video recorded via RGBD cameras. Patients will perform the three tests in the same order used for healthy subjects (Aim #1), i.e., ARAT, BBT, and NHPT. For each test, patients will use the limb contralateral to the impaired limb first, followed by their impaired side. To record patients' UE movements, the inventors will setup the cameras in the optimal configuration determined above. The inventors will give appropriate rest between tasks and tests to prevent fatigue. It is possible that some patients may not be able to perform all of the tasks due to the severity of their stroke. In these cases, the physical therapist who administers the test will make the decision to skip those tests.

The accuracy of the CV system can be validated by comparing behavioral features extracted from Mocap and CV systems by using IntraClass Correlation (ICC). ICC generates a score between 0 and 1, with 1 denoting identical measurement results. The inventors will assess inter-rater absolute agreement with two-way mixed single measures ICC(3,1) between two raters (CV and Mocap) within each camera configuration group. One inter-rater ICC will be calculated for each of the nine joint RoMs with all measures pooled across 3 tests, 2 sides, and 12 subjects. Additionally, one inter-rater ICC will be calculated for pooled timing features across 2 sides and 12 subjects, for each of the following tests/subtests: Grasp, Grip, and Pinch sub-groups in ARAT, as well as BBT and NHPT. These will result in total 14 ICCs for each camera configuration group. The inventors expect all ICCs to be greater than 0.9 (i.e., excellent agreement) in the best performing group which is defined by the highest average ICC. With an expected ICC of 0.95 and acceptable ICC of 0.9, the inventors estimated that a power >0.8 could be achieved with the proposed number of samples for each ICC calculation.

The CV-extracted behavioral features are then evaluated by objectively comparing them with the clinical assessment scores on their sensitivity to identify motor impairment. The inventors will use unsupervised clustering techniques which automatically group data points based on their similarity. Specifically, for each patient the inventors will create two sets of data: Clinical scores (CS) and Behavioral Features (BF). The CS dataset has four dimensions, each of which represents the standard score of one test. Zero is given if a test is not performed, and each dimension is normalized by its mean and variance. The BF dataset uses features from the impaired side normalized by those extracted from the contralateral side. The rationale is as follows: There might be variability across stroke patients in how they control the limbs due to idiosyncrasies in movement strategies, e.g., one patient may prefer to use shoulder whereas another patient prefers to use elbow, and/or due to biomechanical differences in body segment lengths. Such between-subject variability is generally assumed to be unrelated to the impairments 22,65 and therefore the inventors account for it by normalizing movement features from the impaired side to those from the contralateral side. Given the lack of large body of normative data, the inventors believe that this approach is appropriate. If a patient cannot perform a test, 0 and 100 is given to normalized RoM and timing features, respectively. There are 27 RoM features (9×3 tests) and 21 timing features for ARAT, BBT and NHPT (section 3.3), yielding a BF dataset of 48 dimensions. The inventors will use PCA after normalizing each dimension by its mean and variance to reduce the number of dimensions. By ranking principal components by their total explained variance, the inventors will select the smallest set of PCs to create a reduced BF dataset to account for >95% total variance of the original BF dataset. To identify subgroups from both CS and reduced BF datasets, the inventors will use agglomerative hierarchical clustering 66 with Euclidean distance as similarity metric between subjects. Starting with each subject being a cluster, a dendrogram (i.e., tree structure) can be created by recursively merging clusters based on the inter-cluster similarity with centroid linkage method (i.e., distance between cluster averages). The inventors will determine the number of clusters by maximizing the ratio between the inter-cluster and intra-cluster variation. The inventors predict that the reduced BF dataset will result in more clusters than the CS dataset, therefore demonstrating a greater sensitivity of our CV system to detect patient-specific impairments. More importantly, by combining PCA and clustering analysis, the inventors can compute the contribution of each behavioral feature to the within-cluster similarity for each cluster. This will enable us to identify the top three behavioral features that defines cluster-specific impairment in RoM and timing within each cluster, which can be used for evidence-based clinical decision making.

Thus, the various systems and/or methods disclosed herein provide, among other things, a system and method for markerless motion tracking and for quantification of various aspects of a patient's motion while performing a particular task. Various features and advantages are set forth in the following claims.

What is claimed is:

1. A system for kinematic tracking and assessment of upper extremity function of a patient, the system comprising:
    at least one camera; and
    a controller configured to
        receive a sequence of 2D images captured by the at least one camera, wherein each 2D image in the sequence of 2D images includes at least a portion of a hand and an arm of the patient in a field of view of the 2D image, wherein the sequence of 2D images is captured by the at least one camera while the patient performs an upper extremity function assessment task, and wherein the upper extremity function assessment task includes the patient manipulating at least one physical object,
        automatically detect key points corresponding to anatomical features of the patient in a first 2D image of the sequence of 2D images, automatically determine a position of each key point in 3D space, determine a location of a hand in the first 2D image of the sequence of 2D images, adjust a position, orientation, and finger positions of a three-dimensional virtual model of a hand to match the hand in the first 2D image, determine a position of the at least one physical object in the first 2D image of the sequence of 2D images, track body movements of the patient based on changes in the 3D position of the key points detected in each of a plurality of 2D images in the sequence of images, track hand movements of the patient based on changes in the finger positions of the three-dimensional virtual model determined based on each of the plurality of 2D images in the sequence of images, and track object movements based on changes in the position of the at least one physical object in each of the plurality of 2D images.

2. The system of claim 1, wherein the controller is further configured to calculate one or more quantifiable metrics indicative of upper extremity function of the patient based on at least one selected from a group consisting of the tracked body movements, the tracked hand movements, and the tracked object movements.

3. The system of claim 2, wherein the controller is configured to calculate the one or more quantifiable metrics indicative of upper extremity function of the patient by determining a range of motion of at least one body joint of the patient by determining, for each of the plurality of 2D images, an angle between a first line and a second line in 3D space, the first line extending from a key point indicative of a position of the joint to a second key point indicative of a second anatomical feature of the patient and the second line extending from the key point indicative of the position of the joint to a third key point indicative of a third anatomical feature of the patient, determining a maximum angle value for the joint exhibited in the plurality of 2D images, determining a minimum angle value for the joint exhibited in the plurality of 2D images, and defining the range of motion for the joint based on a difference between the maximum angle value for the joint and the minimum angle value for the joint.

4. The system of claim 3, wherein the key point indicative of a position of the joint is a key point indicative of a position of an elbow of the patient, wherein the second key point is a key point indicative of a position of a shoulder of the patient, and wherein the third key point is a key point indicative of a position of a wrist or a hand of the patient.

5. The system of claim 2, wherein the controller is configured to calculate the one or more quantifiable metrics indicative of upper extremity function of the patient by quantifying a degree of finger synergy indicative of a covariance of movements of a plurality of finger joints based on tracked movements of the three-dimensional virtual model of the hand, wherein the finger synergy is indicative of coordinated finger movements in gripping or releasing the at least one physical object.

6. The system of claim 2, wherein the controller is configured to calculate the one or more quantifiable metrics indicative of upper extremity function of the patient by identifying action timings associated with particular actions performed by the patient while performing the upper extremity function assessment task, wherein the particular actions include at least one selected from a group consisting of the hand of the patient gripping the at least one physical object, moving the at least one physical object from a first position to a second position, the hand of the patient releasing the at least one physical object, and moving the hand of the patient without holding the at least one physical object.

7. The system of claim 6, wherein the controller is configured to determine an action timing associated with moving the at least one physical object from the first position to the second position in response to detecting coordinated movements of the hand of the patient and the at least one physical object.

8. The system of claim 6, wherein the controller is configured to determine an action timing associated with releasing the at least one physical object in response to detecting at least one selected from a group consisting of a movement of the at least one physical object that does not coordinate with a movement of the hand of the patient after detecting coordinated movement between the hand of the patient and the at least one physical object, and a finger synergy indicative of a hand movement where the joint angles of the fingers increase.

9. The system of claim 2, wherein the controller is configured to determine a plurality of quantifiable metrics indicative of upper extremity function of the patient, and wherein the controller is further configured to identify, based on the plurality of quantifiable metrics, at least one particular aspect of upper extremity function that exhibits significant impairment, and generate an output to a user identifying the at least one particular aspect of upper extremity function that exhibits significant impairment.

10. The system of claim 9, wherein the controller is configured to determine the plurality of quantifiable metrics indicative of upper extremity function of the patient for a first arm of the patient and a second arm of the patient, wherein the first arm exhibits greater impairment than the second arm, and wherein the controller is configured to identify at least one particular aspect of upper extremity function that exhibit significant impairment by quantifying a degree of impairment for each of a plurality of aspects of upper extremity function based at least in part of a ratio of a quantifiable metric indicative of an aspect of upper extremity function for the first arm relative to the quantifiable metric indicative of the same aspect of upper extremity function for the second arm, and identifying at least one aspect of upper extremity function with a highest quantified degree of impairment based at least in part on the ratios.

11. A method of assessing upper extremity function of a patient, the method comprising:

capturing a sequence of 2D images by each of at least one camera, wherein each 2D image in the sequence of 2D images includes at least a portion of a hand and an arm of the patient in a field of view of the 2D image, wherein the sequence of 2D images is captured by the at least one camera while the patient performs an upper extremity function assessment task, and wherein the upper extremity function assessment task includes the patient manipulating at least one physical object, automatically detecting, by an electronic processor, key points corresponding to anatomical features of the patient in a first 2D image of the sequence of 2D images, automatically determining, by the electronic processor, a position of each key point in 3D space, determining a location of a hand in the first 2D image of the sequence of 2D images, adjusting, by the electronic processor, a position, orientation, and finger positions of a three-dimensional virtual model of a hand to match the hand in the first 2D image, determining, by the electronic processor, a position of the at least one physical object in the first 2D image of the sequence of 2D images, tracking body movements of the patient based on changes in the 3D position of the key points detected in each of a plurality of 2D images in the sequence of images, tracking hand movements of the patient based on changes in the finger positions of the three-dimensional virtual model determined based on each of the plurality of 2D images in the sequence of images, and tracking object movements based on changes in the position of the at least one physical object in each of the plurality of 2D images.

12. The method of claim 11, further comprising calculating one or more quantifiable metrics indicative of upper extremity function of the patient based on at least one selected from a group consisting of the tracked body movements, the tracked hand movements, and the tracked object movements.

13. The method of claim 12, wherein calculating the one or more quantifiable metrics indicative of upper extremity function of the patient includes determining a range of motion of at least one body joint of the patient by determining, for each of the plurality of 2D images, an angle between a first line and a second line in 3D space, the first line extending from a key point indicative of a position of the joint to a second key point indicative of a second anatomical feature of the patient and the second line extending from the key point indicative of the position of the joint to a third key point indicative of a third anatomical feature of the patient, determining a maximum angle value for the joint exhibited in the plurality of 2D images, determining a minimum angle value for the joint exhibited in the plurality of 2D images, and defining the range of motion for the joint based on a difference between the maximum angle value for the joint and the minimum angle value for the joint.

14. The method of claim 13, wherein the key point indicative of a position of the joint is a key point indicative of a position of an elbow of the patient, wherein the second key point is a key point indicative of a position of a shoulder of the patient, and wherein the third key point is a key point indicative of a position of a wrist or a hand of the patient.

15. The method of claim 12, wherein calculating the one or more quantifiable metrics indicative of upper extremity function of the patient includes quantifying a degree of finger synergy indicative of a covariance of movements of a plurality of finger joints based on tracked movements of the three-dimensional virtual model of the hand, wherein the finger synergy is indicative of coordinated finger movements in gripping or releasing the at least one physical object.

16. The method of claim 12, wherein calculating the one or more quantifiable metrics indicative of upper extremity function of the patient includes identifying action timings associated with particular actions performed by the patient while performing the upper extremity function assessment task, wherein the particular actions include at least one selected from a group consisting of the hand of the patient gripping the at least one physical object, moving the at least one physical object from a first position to a second position, the hand of the patient releasing the at least one physical object, and moving the hand of the patient without holding the at least one physical object.

17. The method of claim 16, wherein identifying the action timings includes determining an action timing associated with moving the at least one physical object from the first position to the second position in response to detecting coordinated movements of the hand of the patient and the at least one physical object.

18. The method of claim 16, wherein identifying the action timings includes determining an action timing associated with releasing the at least one physical object in response to detecting at least one selected from a group consisting of a movement of the at least one physical object that does not coordinate with a movement of the hand of the patient after detecting coordinated movement between the hand of the patient and the at least one physical object, and a finger synergy indicative of a hand movement where the joint angles of the fingers increase.

19. The method of claim 12, wherein calculating one or more quantifiable metrics includes determining a plurality of quantifiable metrics indicative of upper extremity function of the patient, and the method further comprising:

identifying, based on the plurality of quantifiable metrics, at least one particular aspect of upper extremity function that exhibits significant impairment, and generating an output to a user identifying the at least one particular aspect of upper extremity function that exhibits significant impairment.

20. The method of claim 19, wherein determining the plurality of quantifiable metrics includes determining the plurality of quantifiable metrics indicative of upper extremity function of the patient for a first arm of the patient and a second arm of the patient, wherein the first arm exhibits greater impairment than the second arm, and wherein identifying at least one particular aspect of upper extremity function that exhibit significant impairment includes quantifying a degree of impairment for each of a plurality of aspects of upper extremity function based at least in part of a ratio of a quantifiable metric indicative of an aspect of upper extremity function for the first arm relative to the quantifiable metric indicative of the same aspect of upper extremity function for the second arm, and identifying at least one aspect of upper extremity function with a highest quantified degree of impairment based at least in part on the ratios.

* * * * *